United States Patent
Al-Sayari et al.

(10) Patent No.: US 9,512,055 B1
(45) Date of Patent: Dec. 6, 2016

(54) DIRECT OXIDATION OF METHANE TO FORMALDEHYDE AND METHANOL

(71) Applicant: Najran University, Najran (SA)

(72) Inventors: Saleh A. Al-Sayari, Najran (SA); Adel A. Ismail, Najran (SA); Cristina Valero, Najran (SA); Maria Consuelo Alvarez-Galvan, Najran (SA); Sergio Garcia, Najran (SA); Jose L. G. Fierro, Najran (SA)

(73) Assignee: NAJRAN UNIVERSITY, Najran (SA)

( * ) Notice: Subject to any disclaimer, the term of this patent is extended or adjusted under 35 U.S.C. 154(b) by 0 days.

(21) Appl. No.: 14/807,715

(22) Filed: Jul. 23, 2015

Related U.S. Application Data

(60) Provisional application No. 62/028,697, filed on Jul. 24, 2014.

(51) Int. Cl.
  *C07C 45/73* (2006.01)
  *C07C 29/50* (2006.01)
  *C07C 45/33* (2006.01)

(52) U.S. Cl.
  CPC .............. *C07C 45/33* (2013.01); *C07C 29/50* (2013.01)

(58) Field of Classification Search
  CPC .................................. C07C 45/33; C07C 29/50
  USPC ........................................ 568/469, 470, 910
  See application file for complete search history.

(56) References Cited

PUBLICATIONS

Gesser et al., Catal. Today, 1998, 42, 183-189.
Yarlagadda, et al., Ind. Eng. Chem. Res., 1988, 27, 252-256.
Hunter, et al., Appl. Catal., 1990, 57, 45-54.
Han, et al., Chem. Lett., 1995, 24, 931-932.
Bromly, et al., Comb. Sci. Technol., 1996, 115, 259-296.
Otsuka, et al., Catal. Today, 1998, 45, 23-28.
Otsuka, et al., J. Catal., 1999, 185, 182-191.
Tabata, et al., J. Phys. Chem., 2000, 104, 2648-2654.
Bañares, et al., Catal. Lett., 1998, 56, 149-153.
Tabata et al., Appl. Catal. A: Gen., 2000, 190, 283-289.
Barbero et al., Chem. Commun., 2002, 1184-1185.
Tabata et al., Catal. Rev. Sci. Eng., 2002, 44, 1-58.
Navarro et al., Metal Oxides: Chemistry and Applications, 2006, 463-490, CRC Press, FL, Boca Raton.
Wood et al., J. Catal.. 2004, 225, 300-306.
Launay et al., J. Catal., 2007, 246, 390-398.

*Primary Examiner* — Sikarl Witherspoon
(74) *Attorney, Agent, or Firm* — Cislo & Thomas, LLP

(57) ABSTRACT

A process for the direct oxidation of methane to $C_1$-oxygenates (formaldehyde and methanol) has been developed. The process involves a gas stream, comprising methane, an oxidizing agent (such as air, or oxygen blended with an inert diluent), and a nitrogen oxide as a gas phase sensitizer at oxidation conditions to produce $C_1$-oxygenates, such as formaldehyde and methanol. A certain proportion of nitrogen oxide, which acts as a radical initiator, in the stream is crucial to achieve a high yield of formaldehyde and methanol. In addition, the temperature plays an important role in the conversion of methane and in the selectivity to $C_1$-oxygenates.

22 Claims, No Drawings

DIRECT OXIDATION OF METHANE TO FORMALDEHYDE AND METHANOL

CROSS-REFERENCE TO RELATED APPLICATION

This patent claims the benefit of U.S. Provisional Patent Application Ser. No. 62/028,697, entitled "Direct Oxidation of CH4 to Formaldehyde and Methanol Using Nitrogen Oxides as Gas-phase Initiators," filed Jul. 24, 2014, which application is incorporated in its entirety here by this reference.

TECHNICAL FIELD

This invention relates to a process for converting methane to $C_1$-oxygenates (formaldehyde and methanol) and more specifically in a single step, by contacting methane, an oxidizing agent (such as air, or oxygen diluted with an inert diluent), and nitrogen oxide in a small proportion at oxidation conditions.

BACKGROUND

Today, both chemical and energy industries rely on petroleum as the principal source of carbon products and energy. However, petroleum energy is under-used because of the remote locations of methane reserves, the relatively high transportation costs, and the thermodynamic and kinetic stability of this energy and chemical resource. Currently, the conversion of natural gas in fuels and chemical products is a complex and expensive process that requires multiple stages, and the main industrial use of methane is in the production of synthesis gas via steam reforming, a highly endothermic process. Synthetic gas in turn is converted to methanol at elevated pressures. Finally, formaldehyde would be obtained by oxidation of methanol at high pressure.

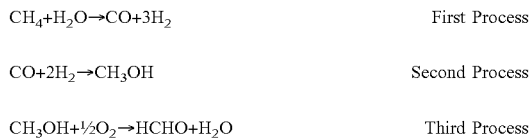

| | |
|---|---|
| $CH_4 + H_2O \rightarrow CO + 3H_2$ | First Process |
| $CO + 2H_2 \rightarrow CH_3OH$ | Second Process |
| $CH_3OH + \frac{1}{2}O_2 \rightarrow HCHO + H_2O$ | Third Process |

The production of methanol is important because methanol can be used to produce other important chemicals such as olefins, acetic acetate, acetate esters, and polymer intermediates. Thus, a direct conversion of methane into methanol and formaldehyde would be highly attractive compared to the current process that is expensive and energy intensive with corresponding environmental impacts.

Selective oxidation of methane has been studied for over 35 years by individuals as well as academic and government researchers with no commercial success. The direct route for methane conversion has remained one of the major scientific and technological challenges, since the catalytic activity and selectivity to $C_1$-oxygenates are still far from a possible industrial application.

The direct conversion of methane into valuable chemicals, i.e., $CH_3OH$ and $HCHO$, involves partial oxidation under fuel rich conditions, i.e., $O_2:CH_4$ molar ratio is below 0.5. The use of fuel-rich mixtures with an oxidant minimizes the extent of combustion reactions, which yield unwanted carbon oxides. Under these conditions, purely gas-phase oxidation reactions require high temperatures, which are detrimental for the control of selectivity of the desired products. Accordingly, considerable efforts have been made in the last fifteen years to develop active and selective catalysts and reactor configurations for the partial oxidation of methane. For example, some articles (Gesser et al., *Catal. Today*, 1998, 42, 183-189; Yarlagadda, et al., *Ind. Eng. Chem. Res.*, 1988, 27, 252-256; and Hunter, et al., *Appl. Catal.*, 1990, 57, 45-54) disclose that reactor inertness is the key ingredient for obtaining high methanol selectivity and that a glass-lined reactor gives the highest selectivity to methanol and formaldehyde. Thermodynamic and kinetic studies reveal that the rate-limiting step of the partial oxidation of methane is the first H-abstraction from the C—H bond. Thus, initiators and sensitizers have been examined in order to decrease the energy barrier of this H-abstraction.

Several authors (Han, et al., *Chem. Lett.*, 1995, 24, 931-932; Bromly, et al., *Comb. Sci. Technol.*, 1996, 115, 259-296; Otsuka, et al., *Catal. Today*, 1998, 45, 23-28; Otsuka, et al., *J. Catal.*, 1999, 185, 182-191; Tabata, et al., *J. Phys. Chem.*, 2000, 104, 2648-2654; Bañares, et al., *Catal. Lett.*, 1998, 56, 149-153) claim that nitrogen oxides promote gas-phase reactions with methane. Based on thermodynamic considerations, in Bromly, et al., *Comb. Sci. Technol.*, 1996, 115, 259-296; Otsuka, et al., *Catal. Today*, 1998, 45, 23-28, kinetic models for the $CH_4+NO+O_2$ reaction were developed. The predictions of these kinetic models afforded excellent descriptions of the experimental data, obtained at atmospheric pressure, over the entire range explored. In these contributions, it was claimed that CO is the oxidation product but in no case were HCHO or $CH_3OH$ recorded as oxidation products. Tabata et al., *Appl. Catal., A: Gen.*, 2000, 190, 283 proposed a reaction model for the conversion of $CH_4$ to $CH_3OH$ and HCHO using either $NO_x$ (x=1, 2), or $NO_2+O_2$ as oxidant agents. Specifically, the calculated transition barrier of H-abstraction from the $CH_4$ of the reaction $CH_4+NO_2 \rightarrow CH_3+HNO_2$ was lower than that for the reaction $CH_4+O_2 \rightarrow CH_3+HO_2$. The decrease in the transition barrier was experimentally verified by the linear enhancement of $CH_4$ conversion with the $NO_2$ concentration in the $CH_4+O_2+NO_2$ mixture, and the experimental results of selectivity to $C_1$-oxygenates were satisfactorily described by using the calculated values of the transition barriers and rate constants of the selected reaction routes from the methoxide radical ($CH_3O$) to $CH_3OH$ and HCHO.

Literature survey reveals that transition oxides of copper (Cu), vanadium (V), molybdenum (Mo), iron (Fe), cobalt (Co), and some multi-component catalysts supported on various carriers are generally used as catalysts for such partial oxidations in the gas phase (Barbero et al., *Chem. Commun.*, 2002, 1184-1185; Tabata et al., *Catal. Rev. Sci. Eng.*, 2002, 44, 1-58; and Navarro et al., *Metal Oxides: Chemistry and Applications*, 2006, 463-490, CRC Press, Fla., Boca Raton). Using ZSM-5 zeolite as a carrier and $Fe_3^+$ oxide as a redox oxide, methane is oxidized in the presence of $N_2O$ gas to produce methanol. Wood, et al., *J. Catal.*, 2004, 225, 300-306 discloses the methanol formation reactions on Fe/Al-ZSM-5 via the oxidation of methane by nitrous oxide, with methanol selectivity less than 2% at reaction temperatures above 250° C. This work also claims that when $H_2O$ is introduced at these reaction temperatures, the rate of methanol formation from the surface methoxy species increases. Water was added to the catalyst after formation of surface radicals, which are generated with interaction of $N_2O$ and $CH_4$ on a catalyst surface. Mesoporous $VO_x/SiO_2$ catalysts have been used with the high efficiency of mesoporous $VO_x/SiO_2$ catalysts for selective partial oxidation of methane to formaldehyde (Launay et al., *J.Catal.*, 2007, 246, 390).

Obtained results verify the success of a reaction conducted by a homogenous process promoted by the use of a nitrogen oxide in a certain proportion, together with methane and an oxidizing agent (such as air, or oxygen diluted with an inert diluent). Applicants have also developed a process that achieves the selective oxidation of methane to $C_1$-oxygenates without the use of a catalyst.

SUMMARY

The present invention is directed to a process for converting methane to formaldehyde and methanol by contacting, at a certain pressure and temperature, a gas stream comprising methane, an oxidizing agent (such as air, or oxygen diluted with an inert diluent), and a low concentration of nitrogen oxide. The process may utilize different catalytic systems, based on several active phases and supports. Another object of the invention is related to the optimization of the reaction conditions such as the reaction temperature, nitrogen oxide type, nitrogen oxide concentration, and proportion of the inert diluent.

These and other features, aspects, and advantages of the present invention will become better understood with reference to the following description and appended claims.

DETAILED DESCRIPTION OF THE INVENTION

The detailed description set forth below is intended as a description of presently -preferred embodiments of the invention and is not intended to represent the only forms in which the present invention may be constructed or utilized. The description sets forth the functions and the sequence of steps for constructing and operating the invention. It is to be understood, however, that the same or equivalent functions and sequences may be accomplished by different embodiments that are also intended to be encompassed within the spirit and scope of the invention.

The present invention relates to a process for the oxidation of methane to formaldehyde and methanol by reaction with an oxidizing agent (such as air, or oxygen diluted with an inert diluent), and a gas phase sensitizer, preferably a nitrogen oxide (e.g., NO, $NO_2$, $N_2O$, or mixtures thereof). The process may be set at a temperature between 300° C. and 800° C., with a pressure between about 101 kPa to about 1010 kPa, with a contact time between about 1 minute to about 24 hours, and a nitrogen oxide concentration between about 0.01 mol% and about 10 mol%.

In the preferred embodiment, the methane, oxidizing agent, and nitrogen oxide are added independently to a fixed bed reactor and are flowed through the fixed bed reactor in a continuous mode. Preferably, the methane/oxidizing agent/ nitrogen oxide mixture is flowed through the fixed bed reactor at a gas hourly space velocity (GHSV) of about 100 $h^{-1}$ to about 100,000 $h^{-1}$. Outlet gas stream leaves the reactor continuously and it is analyzed by gas chromatography (GC).

In the preferred embodiment, the oxidizing agent comprises oxygen and an inert diluent, wherein the inert diluent is any one or more of a gas selected from the group consisting of nitrogen, argon, and helium. The methane-to-oxygen molar ratio is preferably from about 1.5 to about 2.5 and the inert diluent-to-oxygen molar ratio is preferably from about 2 to about 6.

In some embodiments, catalysts may be used. The catalysts used comprise a transition metal compound in the oxide form comprising an active phase, wherein the active phase is a redox oxide, such as $MoO_3$, $V_2O_5$, $WO_3$, or CuO or a basic oxide such as BaO, MgO, or SrO. In the preferred embodiment, the selected transition metal compound is present in an amount from about 0.1 wt % to about 10 wt % of the catalyst.

The catalysts may be formed on a support in the fixed bed reactor. The support may be selected from a group of different base metal oxides, which include but are not limited to alumina (in different phases), silica, titania, zirconia, and zeolites, such as ZSM-5 or Yttrium (Y).

The transition metal compound may be deposited onto the support by methods well known in the art, which include wet impregnation, ion exchange, precipitation, sol-gel, etc. Wet impregnation and ion exchange are carried out by preparing a solution of the transition metal compound in water and then contacting the support with the solution for a time sufficient to adsorb or ion exchange (in the case of a zeolite substrate) the transition metal compound onto the support. The solution for the transition metal compound may include, but are not limited to, ammonium vanadate, ammonium molybdate, and copper acetate. Water is the solvent that is usually used to prepare the solution; however, organic solvents such as ethanol, methanol, or acetone can be used. Once the transition metal compound is adsorbed onto the support, it is dried and then calcined in two stages at a temperature of about 200° C. to about 800° C. for a time of about 1 hour to about 24 hours. Depending on the support, the catalyst may be present on the support as a metal cation or a metal oxide.

The catalyst performance for the partial oxidation of methane may be evaluated on a fixed bed quartz reactor (10 mm ID, 23 cm length) placed inside a vertical furnace and fed from the top. The catalyst may be placed between quartz wool plugs in the middle of the fixed bed quartz reactor, forming a catalyst bed. The temperature of the catalyst bed may be measured by a thermocouple located inside a coaxially-centered quartz cover. One exemplary parameter setting comprises a catalyst sample of 0.10 g, a $N_2$:$CH_4$:$O_2$ molar ratio from about 3.8:1.9:1.0 to about 4.4:1.9:1.0, a pressure of about 101 kPa to about 1010 kPa, and a space velocity (GHSV) of about 100 $h^{-1}$ to about 100000 $h^{-1}$. In addition, several nitrogen oxide concentrations, from about 0.01 mol% to about 10 mol%, may be used while maintaining the oxygen and methane concentrations constant. Nitrogen may be used to balance the variation of nitrogen oxide. Four separate lines or feed streams for methane, nitrogen, oxygen, and nitrogen oxide may be used. Flow rates were adjusted by mass flow controllers and all gases may be mixed prior to reaching the reactor containing the catalyst. The effluents of the reactor and feed streams may be analyzed by a GC fitted with a thermal conductivity detector, using a Porapak Q, 4A molecular sieve columns, and helium as a carrier gas. The outlet of the reactor to the injection port of GC may be heated up to 150° C. in order to avoid water condensation and formaldehyde polymerization.

EXAMPLES

A series of experiments were conducted to investigate the activity of various catalysts at various temperatures and with and without added nitrogen oxide. Catalyst samples of 0.10 g were placed in a quartz reactor of 10 mm ID with a $N_2$:$CH_4$:$O_2$ molar ratio from about 3.8:1.9:1 to about 4.4: 1.9:1 and an inlet total flow rate of 16.1 $mL_N$/min at atmospheric pressure with temperatures between 300° C. to 800° C. Nitrogen oxide concentrations between 0.01 mol% and 10 mol% were used while maintaining $CH_4$ and $O_2$ concentrations constant. The effluents from the reactor were analyzed by an on-line GC. Estimated methane conversion and yields toward the different products were calculated based on GC analysis. Results, once the steady state is reached, after around 2 hours, are presented in Tables 1 through 4.

Example 1

The catalyst 0.5 wt % $V_2O_5/SiO_2$ evaluated for the direct partial oxidation of methane to $C_1$-oxygenates in order to study the influence of reaction temperature. The reaction was performed using 1 mol% of NO, a $N_2:CH_4:O_2$ molar ratio of 4.4:1.9:1.0, and an inlet total flow of 16.1 $mL_N$/min. Obtained results (Table 1) reveal an increase in methane conversion and in $C_1$-oxygenates yield with reaction temperature, with the maximum being found at 650° C.

TABLE 1

Effect of temperature for catalyst $V_2O_5$—$SiO_2$

| Temperature (° C.) | Conversion $CH_4$ (%) | Yield HCHO (%) | Yield $CH_3OH$ (%) | Yield CO (%) | Yield $CO_2$ (%) |
|---|---|---|---|---|---|
| 440 | 0.5 | 0.4 | 0 | 0.1 | 0 |
| 510 | 2 | 0.6 | 0 | 1.1 | 0.3 |
| 580 | 5.2 | 1.2 | 0 | 3.5 | 0.5 |
| 650 | 31.8 | 2.6 | 0.1 | 22.1 | 7 |

Example 2

The catalysts 0.5 wt % $V_2O_5/SiO$, 0.5 wt % $MoO_3/SiO_2$, and 0.5 wt % Cu/ZSM-5 were evaluated for the direct partial oxidation of methane to $C_1$-oxygenates in order to study the catalyst composition.

The reaction was performed using 1 mol% of NO, a $N_2:CH_4:O_2$ molar ratio of 4.4:1.9:1.0, and an inlet total flow of 16.1 $mL_N$/min at a reaction temperature of 650° C. The amount of catalyst present based on V and Mo oxide was 0.1 g. In the case of the catalyst based on Cu/ZSM-5, with a lower density, the amount of catalyst present was 0.03 g, in order to maintain a similar catalytic bed height and a similar pressure drop. Obtained results (Table 2) reveal a higher activity for the catalyst based on the zeolite since higher methane conversion per unit mass of catalyst was found, but a higher selectivity to carbon dioxide also resulted.

TABLE 2

Influence of catalyst type

| Catalyst | Conversion $CH_4$ (%) | Yield HCHO (%) | Yield $CH_3OH$ (%) | Yield CO (%) | Yield $CO_2$ (%) |
|---|---|---|---|---|---|
| $MoO_3/SiO_2$ | 36.5 | 1.8 | 0.1 | 29.2 | 5.4 |
| Cu/ZSM-5 | 38.2 | 1.2 | 0 | 28.6 | 8.4 |
| $V_2O_5/SiO_2$ method 1 | 34.6 | 2.3 | 0 | 26.3 | 6 |
| $V_2O_5/SiO_2$ method 2 | 31.8 | 2.6 | 0.1 | 22.1 | 7 |

Example 3

The catalyst 0.5 wt % $V_2O_5/SiO_2$ was evaluated for the direct partial oxidation of methane to $C_1$-oxygenates in order to study the influence of nitrogen oxide (NO) concentration. The reaction was performed using a $N_2:CH_4:O_2$ molar ratio of 3.8:1.9:1.0 and an inlet total flow of 16.1 $mL_N$/min at a reaction temperature of 650° C. The amount of catalyst present was 0.1 g. With the above conditions, obtained results (Table 3) reveal an increase in the yield to $C_1$-oxygenates with the increase of the concentration of nitrogen oxide (NO). The dramatic increase of methane conversion with NO concentrations higher than 340 ppm is mainly due to an increase in the selectivity to more oxidized compounds (CO and $CO_2$).

TABLE 3

Influence of NO concentration (for 0.5 wt % V2O5/SiO2)

| NO (ppm) | Conversion $CH_4$ (%) | Yield HCHO (%) | Yield $CH_3OH$ (%) | Yield CO (%) | Yield $CO_2$ (%) |
|---|---|---|---|---|---|
| 0 | 1.5 | 0.2 | 0 | 0.8 | 0.5 |
| 340 | 12.2 | 0.5 | 0 | 9.4 | 2.3 |
| 1,100 | 21.2 | 1.4 | 0 | 17.2 | 2.6 |
| 3,356 | 30.5 | 2.2 | 0 | 19.6 | 8.7 |
| 10,000 | 31.8 | 2.6 | 0.1 | 22 | 7.1 |

Example 4

The homogeneous reaction for the direct partial oxidation of methane to $C_1$-oxygenates was evaluated without any catalyst, in order to study the influence of the presence of nitrogen oxide (NO) in the feed (10,000 ppm). The reaction was performed using a $N_2:CH_4:O_2$ molar ratio of 4.4:1.9:1.0 and an inlet total flow of 16.1 $mL_N$/min at a reaction temperature of 650° C. In the above conditions, obtained results (Table 4) reveal that the presence of NO in the feed is crucial to achieve high $CH_4$ conversion, wherein higher selectivity to $C_1$-oxygenates results when certain catalysts are used. A decrease in the yield toward $C_1$-oxygenates is found with some other catalysts. This fact would point to an oxidation of part of formaldehyde and methanol molecules to carbon monoxide and carbon dioxide when these $C_1$-oxygenates are activated in the catalyst surface. The dramatic increase of methane conversion with NO is explained by a radical mechanism by which nitrogen oxide acts as an initiator.

TABLE 4A

Influence of NO in blank reactor

| NO (ppm) | Conversion $CH_4$ (%) | Yield HCHO (%) | Yield $CH_3OH$ (%) | Yield CO (%) | Yield $CO_2$ (%) |
|---|---|---|---|---|---|
| 0 | 0.5 | 0 | 0 | 0 | 0.5 |
| 10,000 | 26.8 | 1.3 | 0 | 23.2 | 2.3 |

TABLE 4B

Influence of NO in blank reactor

| T (°C.) | NO (ppm) | Molar ratio $N_2:O_2:CH_4$ | $Q_{in}$ ($mL_N$/min) | $Q_{out}$ ($mL_N$/min) | $XCH_4$ (%) | $XO_2$ (%) | Selectivity to C prod. | | | |
|---|---|---|---|---|---|---|---|---|---|---|
| | | | | | | | $CH_2O$ | $CH_3OH$ | CO | $CO_2$ |
| 650 | 0 | 18:1:1.9 | 14.5 | 16.4 | 0.5 | 37.9 | 0.2 | 0 | 0.2 | 0.1 |
| 650 | 10,000 | 4.4:1:1.9 | 16.1 | 15.2 | 26.8 | 90.4 | 2.6 | 0.1 | 20.7 | 3.4 |

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A process for converting methane to formaldehyde and methanol in a single step, comprising contacting a mixture of gases comprising methane, oxygen, nitrogen, and a nitrogen oxide, the nitrogen oxide present at about 1 molar percent of the mixture of gases, wherein the process is continuous and set at a temperature of about 650° C., with atmospheric pressure, and a contact time of about 2 hours, wherein the mixture of gases has a $N_2:CH_4:O_2$ molar ratio from about 3.8:1.9:1.0 to about 4.4:1.9:1.0, wherein methane, oxygen, nitrogen, and the nitrogen oxide concentration are fed into a fixed bed reactor independently and the mixture of gases is continuously flowed through a catalyst bed in the fixed bed quartz reactor with an approximately 10 mm internal diameter (ID) and an approximately 23 cm length, an inlet total flow of about 16.1 $mL_N$/minute, and wherein the catalyst is selected from the group consisting of 0.5 wt % $V_2O_5/SiO_2$, 0.5 w % $MoO_3/SiO_2$, and 0.5 wt % Cu/ZSM-5.

2. A process for converting methane to formaldehyde and methanol in a single step, comprising contacting a mixture of gases comprising methane, an inert diluent, and a nitrogen oxide, the nitrogen oxide present at about 1 molar percent of the mixture of gases, wherein the process is continuous and set at a temperature of about 300° C. to about 800° C., with atmospheric pressure, and a contact time of about 1 minute to about 24 hours, wherein the mixture of gases has a methane-to-oxygen molar ratio about 1.5:1 to about 2.5:1 and an inert diluent-to-oxygen molar ratio from about 2:1 to about 6:1, and wherein methane, the inert diluent, and the nitrogen oxide concentration are fed into a fixed bed reactor, with an approximately 10 mm internal diameter (ID) and an approximately 23 cm length, independently and the mixture of gases is continuously flowed through the fixed bed reactor.

3. A process for converting methane to formaldehyde and methanol in a single step, comprising continuously contacting a mixture of gases comprising methane, an oxidizing agent, and a nitrogen oxide, wherein methane, an inert diluent, and the nitrogen oxide concentration are fed into a fixed bed quartz reactor, with an approximately 10 mm internal diameter (ID) and an approximately 23 cm length, independently and the mixture of gases is continuously flowed through the fixed bed reactor.

4. The process of claim 3 wherein the nitrogen oxide present at a molar percentage of about 0.01 to about 10 of the mixture of gases.

5. The process of claim 3 wherein the process is set at a temperature of about 300° C. to about 800° C.

6. The process of claim 3 wherein the process is set at a pressure of about 101 kPa to about 1010 kPa.

7. The process of claim 3 wherein the process is set at contact time of about 1 minute to about 24 hours.

8. The process of claim 3 wherein the oxidizing agent is air.

9. The process of claim 3 wherein the oxidizing agent comprises oxygen and an inert diluent.

10. The process of claim 9 wherein the inert diluent is any one or more of a gas selected from the group consisting of nitrogen, argon, and helium.

11. The process of claim 9 wherein the mixture of gases has a methane-to-oxygen molar ratio from about 1.5:1 to about 2.5:1.

12. The process of claim 9 wherein the mixture of gases has an inert diluent-to-oxygen molar ratio from about 2:1 to about 6:1.

13. The process of claim 9 wherein inert diluent is nitrogen.

14. The process of claim 13 wherein methane, oxygen, nitrogen, and the nitrogen oxide are fed into the fixed bed quartz reactor independently.

15. The process of claim 14 wherein a catalyst placed on a catalyst bed in the fixed bed reactor and the mixture of gases is continuously flow through the catalyst bed.

16. The process of claim 15 wherein the mixture of gases is flowed through the catalyst bed at a gas hourly space velocity (GHSV) of about 100 $h^{-1}$ to about 100,000 $h^{-1}$.

17. The process of claim 15 wherein the catalyst is prepared using a support comprising oxides selected from the group consisting of $Al_2O_3$, $SiO_2$, $TiO_2$, $ZrO_2$, and zeolites.

18. The process of claim 17 wherein the zeolites is selected from the group consisting of ZSM-5 and Y.

19. The process of claim 15 wherein the catalyst is prepared with a transitional metal compound selected from the group consisting of redox oxides and basic oxides.

20. The process of claim 19 wherein the transitional metal compound is selected from the group consisting of redox oxides $MoO_3$, $V_2O_5$, $WO_3$, and CuO.

21. The process of claim 19 wherein the transitional metal compound is selected from the group consisting of basic oxides BaO, MgO, and SrO.

22. The process of claim 15 wherein the catalyst is selected from the group consisting of 0.5 wt % $V_2O_5/SiO_2$, 0.5 wt % $MoO_3/SiO_2$, and 0.5 wt % Cu/ZSM-5.

* * * * *